(12) United States Patent
Kolhe et al.

(10) Patent No.: US 8,900,637 B2
(45) Date of Patent: Dec. 2, 2014

(54) STABLE TASTE MASKED FORMULATIONS OF CEPHALOSPORINS

(75) Inventors: Sachin Pundlik Kolhe, Pune (IN); Subrata Kundu, Pune (IN); Sanjay Chhagan Wagh, Pune (IN); Makarand Krishnakumar Avachat, Pune (IN); Himadri Sen, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 1540 days.

(21) Appl. No.: 12/095,767

(22) PCT Filed: Dec. 2, 2005

(86) PCT No.: PCT/IN2005/000394
§ 371 (c)(1),
(2), (4) Date: Oct. 3, 2008

(87) PCT Pub. No.: WO2007/063552
PCT Pub. Date: Jun. 7, 2007

(65) Prior Publication Data
US 2009/0022809 A1   Jan. 22, 2009

(51) Int. Cl.
A61K 9/16 (2006.01)
A61K 31/00 (2006.01)
A61K 9/28 (2006.01)

(52) U.S. Cl.
CPC ............ *A61K 31/00* (2013.01); *A61K 9/1635* (2013.01); *A61K 9/2886* (2013.01)
USPC ............ 424/494; 424/493; 424/498; 424/490

(58) Field of Classification Search
USPC ...................................................... 424/494
See application file for complete search history.

(56) References Cited

U.S. PATENT DOCUMENTS

| 4,562,181 | A | * | 12/1985 | Crisp et al. ............... 514/202 |
| 4,865,851 | A | * | 9/1989 | James et al. ............... 424/498 |
| 5,079,007 | A | * | 1/1992 | Putnam .................... 424/422 |
| 5,677,443 | A | * | 10/1997 | Zenoni et al. ............ 540/215 |
| 5,945,124 | A | * | 8/1999 | Sachs et al. ............... 424/472 |
| 6,323,193 | B1 | | 11/2001 | Somani et al. |
| 6,346,530 | B1 | | 2/2002 | Somani et al. |
| 2004/0157826 | A1 | * | 8/2004 | Lampilas et al. ........ 514/214.03 |
| 2005/0020572 | A1 | * | 1/2005 | Aszodi et al. ............ 514/214.03 |
| 2005/0208133 | A1 | * | 9/2005 | Tsutsumi et al. ............ 424/472 |

FOREIGN PATENT DOCUMENTS

| WO | WO 00/56286 | 9/2000 |
| WO | WO 02/36126 A1 | 5/2002 |
| WO | WO02/067943 A1 * | 9/2002 ........... A61K 31/545 |

OTHER PUBLICATIONS

Annexes to PCT/IN2005/000394.
International Search Report for PCT/IN2005/000394.
Dhopeshwarkar et al,. "Development of an oral sustained-release antibiotic matrix tablet using in-vitro/in-vivo correlations," *Drug Development and Industrial Pharmacy*, 20:11 (1994). 1851-1867.

* cited by examiner

*Primary Examiner* — Audrea Buckley
(74) *Attorney, Agent, or Firm* — Merchant & Gould P.C.

(57) ABSTRACT

A stable taste masked, pharmaceutical composition comprising a plurality of coated, non-disintegrating discrete dosage units, said units comprising of a core comprising one or more cephalosporins such as cefuroxime axetil and cefpodoxime proxetil and one or more coating layers. Cefuroxime axetil is in α-crystalline and amorphous forms, where at least 30% of the Cefuroxime axetil is in the α-crystalline form, wherein the particle size distribution of the α-crystalline form being such that 100% of the particles have a particle size below 250µ. The ratio of the crystalline fraction to the amorphous fraction ranges from 0.3:0.7 to 0.99:0.01. The particle size of cefpodoxime proxetil is such that 90% of the particles are below 15µ. The process of preparation of coated, non-disintegrating pellets comprising the steps of reducing the particle size of the one or more cephalosporins, blending with the other excipients, wet granulation, extrusion, spheronization, drying and screening to obtain pellets, said pellets being further coated with one or more layers of film coating to achieve taste masking.

27 Claims, No Drawings

STABLE TASTE MASKED FORMULATIONS OF CEPHALOSPORINS

FIELD OF THE INVENTION

The present invention relates to stable taste masked compositions of cephalosporins.

BACKGROUND OF THE INVENTION

Over the past three decades a variety of antibiotics have become available for clinical use. One class of antibiotics that has seen remarkable growth is the cephalosporins. A majority of the cephalosporins are administered using suspension compositions. However, bitter taste and bioequivalence are major drawbacks of some cephalosporins such as cefuroxime axetil and cefpodoxime proxetil.

U.S. Pat. No. 4,562,181 discloses that cefuroxime axetil can be produced in relatively impure amorphous form or in the form of purer crystalline material. This patent further reveals that substantially pure, crystalline cefuroxime axetil does not have the best balance of properties for commercial use. As per this patent, Cefuroxime axetil is advantageously used in a highly pure, substantially amorphous form. Highly pure cefuroxime axetil when in substantially amorphous form has higher bioavailability upon oral administration than when in crystalline form.

U.S. Pat. No. 4,865,851 discloses that Cefuroxime axetil, both in crystalline form and the amorphous form, has a tendency to form a gelatinous mass when contacted with aqueous media. This gelling effect is temperature dependent but does occur at temperatures of about 37° C., i.e. at the physiological temperatures at which the disintegration of an orally-administered granule would take place. Where there is a relatively slow dispersion of cefuroxime axetil into the surrounding aqueous medium following ingestion, there is the risk that cefuroxime axetil present in the composition may gel. Such gel formation would lead to poor dissolution of the cefuroxime axetil and hence poor absorption from the gastrointestinal tract, i.e. low bioavailability. In the case of granule formulations the use of particles of small diameter and high surface area is desirable to avoid such gelling.

U.S. Pat. No. 4,865,851 also discloses that cefuroxime axetil has an extremely bitter taste which is long lasting and which cannot be adequately masked by the addition of sweeteners and flavors to conventional granule presentations. Cefpodoxime proxetil is a highly hydrophobic, bitter drug that has a tendency to form a gel in aqueous media, which thereby results in slow dissolution and hence poor bioavailability. It is therefore necessary that the pharmaceutical composition be formulated such that bridging of molecules to form a gel is prevented and thereby, the dissolution is improved.

Various investigators have tried different means of overcoming these difficulties.

U.S. Pat. No. 4,865,851 disclose integral lipid coatings as a means of overcoming the extremely bitter taste of cefuroxime axetil and the gelling tendency of Cefuroxime Axetil. However, the process of lipid coating involves the use of specialized equipment such as spray drying apparatus, process criticality and may lead to degradation of the active principle if the proper lipid mixture is not selected. In addition, lipid coating results in extreme variability in the bioavailability of the drug from the suspension formulation.

U.S. Pat. No. 6,346,530 B1 and U.S. Pat. No. 6,323,193 B1 disclose a mixture of amorphous cefuroxime axetil with crystalline cefuroxime axetil such that crystalline cefuroxime axetil forms from about 7 to about 25 weight percent and about 12 to about 25 weight percent respectively of the total amount of amorphous cefuroxime axetil together with crystalline cefuroxime axetil to achieve a comparable bioavailability profile as pure amorphous cefuroxime axetil. These patents disclose the surprising result that it is possible to achieve bioequivalence between formulations comprising of pure amorphous cefuroxime axetil and formulations comprising of up to 25% crystalline cefuroxime axetil.

It would be desirable to have a stable taste masked dosage form, which will address these issues while making use of the less expensive, conventional techniques of making pharmaceutical formulations.

It is now surprisingly found that when cephalosporins are formulated as discrete dosage units such as pellets, the resulting formulations are stable and taste masked.

The present invention is surprising in that such a formulation might be expected to have stability issues due to the stressful processes of preparation and/or bioequivalence issues due to the coating procedures. However, the pharmaceutical compositions of the present invention are not only adequately taste masked but also show satisfactory stability and bioequivalence.

The present inventors have also surprisingly found that contrary to the disclosures in U.S. Pat. No. 4,562,181 and Ranbaxy's patents U.S. Pat. No. 6,346,530 B1 and U.S. Pat. No. 6,323,193 B1, it is possible to make a bioequivalent formulation comprising of substantial quantities of crystalline cefuroxime axetil when the particle size of the crystalline cefuroxime axetil is reduced such that 100% of the particles have a particle size below 250µ.

OBJECTS OF THE INVENTION

An object of the invention is to provide a stable, taste masked pharmaceutical composition comprising a plurality of coated, non-disintegrating discrete dosage units, said units comprising of a core comprising one or more cephalosporin and one or more coating layers.

Another object of the invention is to provide a stable taste masked, pharmaceutical composition comprising a plurality of coated pellets comprising of a core comprising cefuroxime axetil and one or more coating layers.

Another object of the invention is to provide a stable taste masked, pharmaceutical composition comprising a plurality of coated pellets comprising of a core comprising cefuroxime axetil in α-crystalline and amorphous forms and one or more coating layers, wherein at least 30% of the Cefuroxime axetil is in the α-crystalline form, wherein the particle size distribution of the α-crystalline form being such that 100% of the particles have a particle size below 250µ.

Another object of the invention is to provide a stable taste masked, pharmaceutical composition comprising a plurality of coated pellets comprising of a core comprising cefpodoxime proxetil and one or more coating layers.

Another object of the invention is to provide a stable taste masked, pharmaceutical composition comprising a plurality of coated pellets comprising of a core comprising cefpodoxime proxetil and one or more coating layers, wherein the particle size of cefpodoxime proxetil is such that 90% of the particles are below 15µ.

Yet another object of the invention is to provide a process of preparation of coated stable pellets comprising of a core comprising one or more cephalosporin and one or more coating layers, the said process comprising the steps of reducing the particle size of the one or more cephalosporin, blending with the other excipients, wet granulation, extrusion, spheronization, drying and screening to obtain pellets, said pellets being further coated with one or more layers to achieve taste masking.

Another object of the invention is to provide a taste masked, pharmaceutical composition in the form of a plurality of coated, non-disintegrating pellets, said pellets comprising of a core comprising Cefuroxime axetil in α-crystalline and amorphous forms and one or more coating layers, wherein at least 30% of the said Cefuroxime is in the α-crystalline form having a particle size distribution such that 100% of the particles are below 250µ, wherein the said composition demonstrates bioequivalence to the commercially available suspension of Cefuroxime axetil, the said suspension being marketed under the brand name of 'Ceftin®'.

DETAILED DESCRIPTION OF THE INVENTION

The invention pertains to a stable taste masked, pharmaceutical composition in the form of discrete dosage units comprising of a core comprising one or more cephalosporins and one or more coating layers.

The term 'discrete dosage units' comprises pellets, granules, beads, microspheres and ion-exchange resins.

The term "pellets" comprises spherical as well as non-spherical particles prepared by extrusion and spheronization. The latter are also referred to as spheroids.

In a preferred aspect, the invention pertains to a taste masked, pharmaceutical composition in the form of a stable taste masked pellets comprising of a core comprising Cefuroxime axetil and one or more coating layers.

In another preferred aspect, the invention pertains to a taste masked, pharmaceutical composition in the form of stable taste masked pellets comprising of a core comprising cefpodoxime proxetil and one or more coating layers.

The one or more cephalosporins used in the present invention may have any particle size measured by techniques well known to those skilled in the art and which can be achieved using one or more of the methods well known to the persons skilled in the art such as wet milling, dry milling, micronization and controlled crystallization. For example, in a preferred embodiment, the particle size of cefpodoxime proxetil is such that 90% of the particles are below 15µ as measured by Malvern light scattering technique using the wet method.

The term "90% particles below 15µ" as used herein can also be represented as $d_{90}$ of the cefpodoxime particles is below 15µ. It is noted that the notation $d_x$ means that X % of particles have a diameter less than the specified diameter D.

These pellets comprise of a core comprising of one or more cephalosporins and one or more excipients selected from the group comprising of diluents, stabilizers, binders, disintegrants, glidants, lubricants and flow aids, wetting agents and the like. One excipient can perform more than one function.

Diluents, which include, but are not limited to mannitol, sucrose, starch, lactose, dicalcium phosphate, xylitol, sorbitol, micro-crystalline cellulose and the like can be used.

One or more organic acids can be used in the pellet composition as a stabilizer. The stabilizer reduces the impurity levels of the compositions and thus contributes to the stability of these compositions. Examples of suitable organic acids include, but are not limited to oxalic acid, citric acid, tartaric acid, maleic acid and the like. While any amount of the one or more organic acids can be used provided it stabilizes the one or more cephalosporins, in a preferred embodiment, 1-10% of one or more organic acids can be included in the compositions.

Binders which include, but are not limited to, alkylcelluloses such as methyl cellulose, hydroxyalkylcelluloses such as hydroxypropylcellulose, low substituted hydroxypropylcellulose and hydroxypropyl methylcellulose, sodium carboxymethylcellulose or mixtures thereof, starches, pregelatinised maize starch, sugars or polyvinylpyrrolidone and combinations thereof can be used.

Disintegrants, which include but are not limited to, crospovidone, sodium starch glycolate, starches such as maize starch and dried starch, croscarmellose sodium and cellulose products such as microcrystalline cellulose, microfine cellulose, low substituted hydroxypropylcellulose and the like and combinations thereof.

Glidants, which include, but are not limited to colloidal silica, powdered cellulose, talc, tribasic calcium phosphate and the like can be used.

Lubricants and flow aids such as, but not limited to, stearic acid and its salts as well as its derivatives, calcium silicate and colloidal silicon dioxide can be used.

Wetting agents can include, but are not limited to, surfactants, either singly or in admixture. Examples of surfactants include, but are not limited to, the polysorbates, sodium lauryl sulphate, poloxamers and the like.

All these excipients can be used at levels well known to the persons skilled in the art.

The cores of the invention may be produced by the method of granulation using the one or more cephalosporins together with one or more excipients using conventional techniques. Such granulation techniques include the use of conventional granulators e.g. spray granulators, rotary granulators, centrifugal fluidized bed granulators, high-speed mixer granulators. The wet granules are then extruded and subjected to a process of spheronization. Drying may be carried out by conventional techniques, for example in the granulator or in a drying oven or hot air drier. It is, of course, desirable that the pellets should be prepared by a method, which is convenient to provide pellets of the desired size and shape; this may generally be achieved by conventional adjustment of the conditions of granulation and, if necessary, by screening of the pellets thus produced.

It is, of course, desirable that the pellets should be prepared by a method, which is convenient to provide reproducibility of pellet size distribution, surface area, its smoothness and density of the pellet in addition to reproducibility of morphologic properties of the pellets. This may generally be achieved by conventional adjustment of the conditions of granulation and, if necessary, by screening of the pellets thus produced. Compaction, surface-layering and agglomeration are the pelletisation techniques used in pharmaceutical industries. Of the compaction techniques, extrusion and spheronization is the most popular method as narrower particle size with high capacity output and less cost can be achieved. Recently, however, melt pelletisation has been used frequently to make compaction pellets using a different type of equipment e.g. high-shear mixer. Other pelletisation methods such as globulation, balling and compression are also used but in limited scale. The pellets can also be prepared by other well-known process such as layering over an inert core.

In a preferred embodiment, the pellets can be formed by a process of extrusion through 0.5 mm screen followed by spheronization at an optimum speed of 800-1100 rpm. The resulting pellets are then dried in a fluid bed dryer and then screened to get the pellets of the desired shape and size.

The pellets can further be coated through processes well known to the persons skilled in the art to provide one or more coating layers for the purposes of taste masking and ease of further processing. Conventional coating techniques, for example, spray coating using a fluidized bed granulator, a centrifugal fluidized bed coater or a spray drier or coating with a rotary granulator can be used.

Film-forming agents, which are useful in the coating process, include, but are not limited to, polysaccharides such as maltodextrin, alkyl celluloses such as methyl or ethyl cellulose, hydroxyalkylcelluloses (e.g. hydroxypropylcellulose or hydroxypropylmethylcelluloses e.g. those marketed under the tradename of Methocel®), polyvinylpyrrolidone, polyvinyl alcohol, copolymers of vinylpyrrolidone and vinyl acetate (e.g. marketed under the brand name of Plasdone) and polymers based on methacrylic acid such as those marketed under the brand name of Eudragit and combinations of these. These may be applied from aqueous or non-aqueous systems or combinations of aqueous and non-aqueous systems as appropriate. Additives can be included along with the film formers to obtain satisfactory films. These additives can include plasticizers such as dibutyl phthalate, triethyl citrate, polyethylene glycol and the like, antitacking agents such as talc, stearic acid and its salts as well as its derivatives and colloidal silicon dioxide and the like, surfactants such as polysorbates and sodium lauryl sulphate, coloring agents and opacifying agents such as titanium dioxide and the like. All these excipients can be used at levels well known to the persons skilled in the art.

The pellets can either be administered as such e.g. from a sachet or can further be formulated, along with one or more excipients well known to persons skilled in the art, as a pharmaceutical composition for oral administration such as, but not limited to, tablets, including dispersible tablets, orally disintegrating tablets, hard and soft gelatin capsules or as a suspension composition and the like.

In a preferred embodiment, the pellets can be formulated as a suspension composition along with one or more excipients.

The term "suspension composition" includes within its scope but is not limited to compositions selected from the group of a unit dose packet (sometimes referred to in the art as a "sachet"), in the form of a suspension made from a unit dose packet, in the form of a product for oral suspension for constitution with water or other suitable vehicle before use, in the form of a dose sipping device and in the form of an oral suspension per se. It is noted that when a unit dose packet is constituted, it is probably mainly in the form of a suspension if reconstituted according to directions, although the extent of suspension versus solution depends on a number of factors such as pH. The use of the term "suspension" herein is intended to embrace liquids containing the one or more cephalosporins partially in suspension and partially in solution.

The excipients useful for the suspension composition can be selected from the group consisting of wetting agents, sweeteners, thickening agents, dispersing agents, pH-stabilizing agents, flavouring agents, taste-enhancing agents, preservatives, coloring agents, lubricants and flow aids, antifoaming agents and the like. One excipient can perform more than one function.

Wetting agents can include, but are not limited to, surfactants, either singly or in admixture. Examples of surfactants include, but are not limited to, the polysorbates, sodium lauryl sulphate, poloxamers and the like.

Suitable sweeteners include, but are not limited to, natural sweeteners such as sugars e.g. fructose, glucose, sucrose, sugar alcohols such as mannitol and sorbitol or mixtures thereof and artificial sweeteners such as sodium saccharine, sodium cyclamate and aspartame.

Suitable thickening agents function as suspending agents and include, but are not limited to, hydrocolloid gums known for such purpose, examples of which include xanthan gum, guar gum, locust bean gum, gum tragacanth, and the like and mixtures thereof. Alternatively, synthetic suspending agents may be used such as sodium carboxymethylcellulose, polyvinylpyrrolidone, hydroxypropylcellulose and the like or mixtures thereof.

Dispersing agents include, but are not limited to, colloidal silicon dioxide and surfactants such as sodium lauryl sulphate, polysorbates and the like, wherein the surfactant is used alone or as an admixture with one or more surfactant. Combinations of colloidal silicon dioxide with one or more surfactants can also be used.

The composition may also contain a pH-stabilizing agent to maintain a desired pH upon reconstitution, as discussed above. The term "pH-stabilizing agent" encompasses buffers and pH-altering agents. Suitable pH-stabilizing agents include tribasic sodium phosphate, anhydrous sodium carbonate, glycine, citric acid and the like or mixtures thereof.

Flavoring agents are well known to persons skilled in the art and include, but are not limited to, one or more fruity flavors.

Taste enhancing agents include, but are not limited to, sodium chloride, glycine, citric acid and the like and mixtures thereof.

Suitable preservatives include, but are not limited to, benzoic acid and sorbic acid and their salts, methyl paraben, butylparaben, propylparaben and the like.

Suitable coloring agents include, but are not limited to, titanium dioxide pigments, lake colors and iron oxide pigments.

Lubricants and flow aids such as, but not limited to, talc, stearic acid and its salts as well as its derivatives, calcium silicate and colloidal silicon dioxide can also be used.

Antifoaming agents include, but are not limited to simethicone, dimethyl polysiloxane.

All these excipients can be used at levels well known to the persons skilled in the art.

In a preferred embodiment, a base coating of hydroxypropyl methylcellulose E5 followed by a second coating comprising of aminoalkyl methacrylate copolymer E (Eudragit E 100) and hydroxypropyl methylcellulose E5 can be given to the core pellets comprising one or more cephalosporins.

It is an observed phenomenon that cefuroxime axetil under alkaline conditions shows an increased level of 3 impurity. It was observed that when the pellets comprising cephalosporins were coated alone with aminoalkyl methacrylate copolymer the 3 impurity level increases.

It has been surprisingly found that by coating with aminoalkyl methacrylate copolymer E (Eudragit E 100) along with hydroxypropyl methylcellulose, preferably as subcoat, 3 impurity levels were found to be around 0.2% to 0.3% during coating and 0.65% during stability up to 3 months at 40° C./75% RH condition.

In additional a third outer coating of aminoalkyl methacrylate copolymer E (Eudragit E100) and colloidal silicon dioxide is given in order to prevent agglomeration of pellets. Further this third outer coating helps in achieving taste masking of the dosage form. In a preferred embodiment the taste masking is achieved up to 60 seconds of their contact with liquids.

Further we have surprisingly found that addition of one or more organic acids in the composition of the invention acts as a stabilizer thereby reducing the degradation impurities. Examples of suitable organic acids include, but are not limited to oxalic acid, citric acid, tartaric acid, maleic acid and the like.

In an alternate preferred embodiment, Methacrylic Acid Copolymer, Type A (Eudragit-L 100) can be used directly for coating the pellets.

The coated pellets can be made to be bioequivalent to the existing innovator product by proper selection of excipients and physical forms of the one or more cephalosporins. For example, cefuroxime axetil pellets prepared using the excipients and process of the present invention can be made bioequivalent to the innovator powder for suspension product by proper selection of coating excipients and by proper selection of the ratio of the amorphous form of cefuroxime axetil to the α-crystalline form of cefuroxime axetil and of the particle size of both these forms. For example, the formulation can consist entirely of the α-crystalline form or the amorphous form of cefuroxime axetil. In a preferred embodiment, at least 30% of the cefuroxime axetil used in the formulation is the α-crystalline form, which has a particle size distribution such that 100% of the particles have a size below 250μ. The amorphous form of Cefuroxime axetil constitutes the remaining quantity. Thus, the ratio of the α-crystalline form to the amorphous form can range from 0.3:0.7 to 0.99:0.01. In a still preferred embodiment, the ratio of the α-crystalline form to the amorphous form is 0.3:0.7. The particle size of the α-crystalline form can be reduced using one or more of the methods well known to the persons skilled in the art such as wet milling, dry milling, micronization and controlled crystallization. The particle size of Cefuroxime axetil is measured using Malvern light scattering technique following the dry method. The term "100% particles below 250μ" as used herein can also be represented as $d_{100}$ of the crystalline cefuroxime axetil particles is below 250μ. The following examples are given to demonstrate the invention and are in no way a limitation to the same.

Example 1

| Sr. No. | Ingredients | Quantity for 1 kg batch Example No: | | |
|---|---|---|---|---|
| | | A | B | C |
| Core | | | | |
| 1. | Cefuroxime Axetil (crystalline) | 0.131 kg | 0.131 kg | 0.131 kg |
| 2. | Cefuroxime Axetil (Amorphous) | 0.312 kg | 0.312 kg | 0.312 kg |
| 3. | Microcrystalline cellulose | 0.257 kg | 0.257 kg | 0.257 kg |
| 4. | Carboxymethylcellulose calcium | 0.219 kg | 0.219 kg | 0.219 kg |
| 5. | Citric acid | 0.030 kg | 0.030 kg | 0.030 kg |
| 6. | Hydroxypropyl cellulose | 0.050 kg | 0.050 kg | 0.050 kg |
| 7. | Purified Water | 1.150 lit | 1.150 lit | 1.150 lit |
| 8. | Talc | 0.010 kg | 0.010 kg | 0.010 kg |
| Coating: Sub coat (Coating solution A) | | | | |
| 9. | Hydroxypropylmethylcellulose | 0.080 kg | — | 0.080 kg |
| 10. | Vinyl pyrrolidone/vinyl acetate copolymer (Plasdone S 630) | — | 0.150 kg | — |
| 11. | Methacrylic acid copolymer dispersion (Eudragit L30D55) | — | — | 0.002 kg |
| 12. | Talc | 0.028 kg | 0.017 kg | 0.028 kg |
| 13. | Polyethylene Glycol | 0.008 kg | — | 0.008 kg |
| 14. | Triethyl citrate | — | 0.005 kg | — |
| 15. | Purified Water | 2.400 lit | 3.000 lit | 2.400 lit |
| Coating: Taste masking coat (Coating solution B) | | | | |
| 16. | Aminoalkyl methacrylate copolymer E (Eudragit E 100) | 0.010 kg | 0.010 kg | — |
| 17. | Sodium Lauryl Sulphate | 0.001 kg | 0.001 kg | — |
| 18. | Stearic Acid | 0.001 kg | 0.001 kg | — |
| 19. | Magnesium Stearate | 0.003 kg | 0.003 kg | — |
| 20. | Water | 0.183 lit | 0.183 lit | — |
| 21. | Hydroxypropylmethylcellulose | 0.030 kg | 0.030 kg | — |
| 22. | Talc | 0.015 kg | 0.015 kg | — |
| 23. | Polyethylene Glycol | 0.003 kg | 0.003 kg | — |
| 24. | Water | 1.000 lit | 1.000 lit | — |
| Coating: Outer coat (Coating solution C) | | | | |
| 25. | Aminoalkyl methacrylate copolymer E (Eudragit E 100) | 0.015 kg | 0.015 kg | 0.015 kg |
| 26. | Sodium Lauryl Sulphate | 0.001 kg | 0.001 kg | 0.001 kg |
| 27. | Stearic Acid | 0.002 kg | 0.002 kg | 0.002 kg |
| 28. | Magnesium Stearate | 0.005 kg | 0.005 kg | 0.005 kg |
| 29. | Water | 0.275 lit | 0.275 lit | 0.275 lit |
| 30. | Colloidal silicon dioxide (Aerosil 200) | 0.030 kg | 0.030 kg | 0.030 kg |
| 31. | Water | 1.500 lit | 1.500 lit | 1.500 lit |

Brief Manufacturing Process

1. Sift Cefuroxime Axetil (crystalline and amorphous) through #20 (ASTM) and microcrystalline cellulose and carmellose calcium through #30 (ASTM).
2. Mix all ingredients of Step 1 in planetary mixer.
3. Granulate the mix of Step 2 using a solution of hydroxypropylcellulose and citric acid in water.
4. Extrude the wet mass of Step 3 using extruder through 0.5 mm screen. Spheronize the extruded pellets at 1100 rpm in an spheronizer using talc as antiadherant.
5. Dry the pellets in a fluid bed processor at 40-50° C. till LOD is less than 3% w/w.

6. Coat Step 5 pellets with one or more coating solutions (A), (B) and (C) as applicable sequentially in fluidized bed coater (bottom spray).

Example 2

| Sr. No. | Ingredients | Qty for 1.0 kg batch |
|---|---|---|
| | Core: | |
| 1. | Cefpodoxime proxetil | 0.110 kg |
| 2. | Microcrystalline cellulose | 0.385 kg |
| 3. | Croscarmellose sodium | 0.250 kg |
| 4. | Crospovidone | 0.125 kg |
| 5. | Sodium lauryl sulphate | 0.010 kg |
| 6. | Citric acid | 0.040 kg |
| 7. | Hydroxypropyl cellulose | 0.080 kg |
| 8. | Purified Water | 1.900 lit |
| 9. | Talc | 0.010 kg |
| | Coating: Taste masking coat (Coating solution A) | |
| 10. | Hypromellose 2910 | 0.080 kg |
| 11. | Talc | 0.028 kg |
| 12. | Polyethylene Glycol 6000 | 0.008 kg |
| 13. | Methacrylic acid copolymer dispersion (Eudragit L30D55) | 0.002 kg |
| 14. | Purified Water | 2.400 lit |
| 15. | Water | 1.000 lit |
| | Coating: Outer coat (Coating solution B) | |
| 16. | Aminoalkyl methacrylate copolymer E (Eudragit E 100) | 0.015 kg |
| 17. | Sodium Lauryl Sulphate | 0.001 kg |
| 18. | Stearic Acid | 0.002 kg |
| 19. | Magnesium Stearate | 0.005 kg |
| 20. | Water | 0.275 lit |
| 21. | Colloidal Silicon dioxide | 0.030 kg |
| 22. | Water | 1.500 lit |

Brief Manufacturing Process
1. Sift Cefpodoxime proxetil through #20 (ASTM) and microcrystalline cellulose, croscarmellose sodium and crospovidone through #30 (ASTM).
2. Mix all the ingredients of Step 1 in planetary mixer for 15 minutes.
3. Granulate Step 2 material using a solution of hydroxypropylcellulose and citric acid in water.
4. Extrude the wet mass of Step 3 using extruder through 0.5 mm screen. Spheronize the extruded pellets at 1100 rpm in an spheronizer using talc as antiadherant.
5. Dry the pellets in a fluid bed processor at 40-50° C. till LOD is less than 3% w/w.
6. Coat Step 5 pellets with coating solutions (A) and (B) in fluidized bed coater (bottom spray).

Bioequivalence Studies:
A bioequivalence study was carried out using the pellets of Cefuroxime Axetil of Example 1A against the commercially available oral suspension "Ceftin®" using eight healthy volunteers. The study was monitored in terms of the AUC and $C_{max}$ achieved with the test product and reference product. AUCs are plots of serum concentrations of Cefuroxime Axetil along the ordinate (Y-axis) against time on the abscissa (X-axis). Generally, the values for AUC represent a number of values taken from all the subjects in a population and are, therefore, mean values averaged over the entire population. $C_{max}$, the observed maximum in a plot of serum level concentration of Cefuroxime Axetil (Y-axis) versus time (X-axis) is likewise an average value. The ratios of the log transformed mean values for $C_{max}$ and AUC for the test and reference product (T/R ratio) is a measure of the bioequivalence between the test and reference product. Values between 80 and 125% for the 90% confidence intervals of these ratios indicate bioequivalence as recommended by the US FDA.

Bioequivalence data for the pellets comprising Cefuroxime Axetil against the commercially available suspension formulation "Ceftin®" is shown below in Table 1.

TABLE 1

Fed BE study data of Cefuroxime axetil pellets against commercially available suspension formulation "Ceftin®" n = 8

| PK Parameters | Test product | Reference product | % T/R |
|---|---|---|---|
| Cmax | 2.093 | 2.302 | 90.9 |
| Tmax | 3.588 | 3.040 | — |
| AUC(0-t) | 12.532 | 13.007 | 96.3 |
| AUC(0-∞) | 13.213 | 14.069 | 93.9 |

Test 'T': Cefuroxime Axetil pellets (eq. to 250 mg Cefuroxime Axetil) (Example 1A)
Reference 'R': Ceftin ® 250 mg/5 mL (Cefuroxime Axetil for Oral suspension)

As can be seen from the data above in Table 1, the % T/R ration in case of AUCs and Cmax are well within the limits of 80-125% established by the US FDA for claiming bioequivalence between a test and reference product.

The embodiments of the invention in which an exclusive property or privilege is claimed are defined as follows:

The invention claimed is:

1. A stable taste masked, pharmaceutical composition comprising a plurality of discrete dosage units, each unit comprising a core and one or more coating layers, wherein:
the core comprises cefuroxime axetil in α-crystalline and amorphous forms; and
the composition is a suspension configured to achieve effective antibiotic bioavailability of the cefuroxime axetil upon oral dosing.

2. The pharmaceutical composition of claim 1, wherein the ratio of the crystalline fraction to the amorphous fraction ranges from 0.3:0.7 to 0.99:0.01.

3. A stable taste masked, pharmaceutical composition comprising a plurality of discrete dosage units, each unit comprising a core and one or more coating layers, wherein:
the core comprises cefpodoxime proxetil of particle size such that 90% of these particles are below 15μ;
and the composition is a suspension configured to achieve effective antibiotic bioavailability of the cefpodoxime proxetil upon oral dosing.

4. The pharmaceutical composition of claim 1, wherein the taste masking is achieved up to 60 seconds after oral administration.

5. The pharmaceutical composition of claim 1, wherein the discrete dosage units are selected from beads, granules and pellets.

6. The pharmaceutical composition of claim 1, wherein the discrete dosage units are pellets.

7. The pharmaceutical composition of claim 1, wherein the core further comprises one or more excipients selected from the group consisting of diluents, stabilizers, binders, disintegrants, glidants, lubricants and flow aids, and wetting agents.

8. The pharmaceutical composition of claim 7, wherein the diluent is one or more selected from the group consisting of mannitol, sucrose, starch, lactose, dicalcium phosphate, xylitol, sorbitol, micro-crystalline cellulose.

9. The pharmaceutical composition of claim 7, wherein the stabilizer is one or more selected from the group consisting of oxalic acid, citric acid, tartaric acid and maleic acid.

10. The pharmaceutical composition of claim 7, wherein the binder is one or more selected from the group consisting of alkylcelluloses, hydroxyalkylcelluloses, sodium carboxymethylcellulose, starches, pregelatinised maize starch, sugars and polyvinylpyrrolidone.

11. The pharmaceutical composition of claim 7, wherein the disintegrant is one or more selected from the group consisting of crospovidone, sodium starch glycolate, starches, croscarmellose sodium and cellulose products.

12. The pharmaceutical composition of claim 7, wherein the glidant is one or more selected from the group consisting of colloidal silica, powdered cellulose, talc and tribasic calcium phosphate.

13. The pharmaceutical composition of claim 7, wherein the lubricant and flow aid is one or more selected from the group consisting of stearic acid, salts of stearic acid, derivatives of stearic acid, calcium silicate and colloidal silicon dioxide.

14. The pharmaceutical composition of claim 7, wherein the wetting agent is one or more selected from the group consisting of the polysorbates, sodium lauryl sulphate and poloxamers.

15. The pharmaceutical composition of claim 1, wherein one or more coating layers further comprises of one or more excipients selected from the group consisting of film forming agents, plasticizers, antitacking agents, surfactants, coloring agents and opacifiers.

16. The pharmaceutical composition of claim 15, wherein the film forming agent is one or more selected from the group consisting of polysaccharides, alkyl celluloses, hydroxyalkylcelluloses, polyvinylpyrrolidone, polyvinyl alcohol, copolymers of vinylpyrrolidone and vinyl acetate and polymers based on methacrylic acid.

17. The pharmaceutical composition of claim 15, wherein the plasticizer is one or more selected from the group consisting of dibutyl phthalate, triethyl citrate and polyethylene glycol.

18. The pharmaceutical composition of claim 15, wherein the antitacking agent is one or more selected from the group consisting of talc, stearic acid, salts of stearic acid, derivatives of stearic acid and colloidal silicon dioxide.

19. The pharmaceutical composition of claim 15, wherein the surfactant is one or more selected from the group consisting of polysorbates and sodium lauryl sulphate.

20. The pharmaceutical suspension composition of claim 1, further comprising one or more excipients selected from the group consisting of wetting agents, sweeteners, thickening agents, dispersing agents, pH-stabilizing agents, flavouring agents, taste-enhancing agents, preservatives, coloring agents, lubricants, flow aids, and antifoaming agents.

21. A stable taste masked, pharmaceutical composition according to claim 1, wherein one coating layer comprises aminoalkyl methacrylate copolymer and hydroxypropyl methylcellulose.

22. The pharmaceutical composition of claim 3, wherein the taste masking is achieved up to 60 seconds after oral administration.

23. The pharmaceutical composition of claim 3, wherein the discrete dosage units are selected from beads, granules and pellets.

24. The pharmaceutical composition of claim 3, wherein the discrete dosage units are pellets.

25. The pharmaceutical composition of claim 3, wherein the core further comprises one or more excipients selected from the group consisting of diluents, stabilizers, binders, disintegrants, glidants, lubricants and flow aids, and wetting agents.

26. The pharmaceutical composition of claim 3, wherein one or more coating layers further comprises of one or more excipients selected from the group consisting of film forming agents, plasticizers, antitacking agents, surfactants, coloring agents and opacifiers.

27. The pharmaceutical composition of claim 3, further comprising one or more excipients selected from the group consisting of wetting agents, sweeteners, thickening agents, dispersing agents, pH-stabilizing agents, flavouring agents, taste-enhancing agents, preservatives, coloring agents, lubricants, flow aids, and antifoaming agents.

* * * * *